(12) United States Patent
Imamura et al.

(10) Patent No.: US 9,176,084 B2
(45) Date of Patent: Nov. 3, 2015

(54) GAS SENSOR ELEMENT AND MANUFACTURING METHOD OF THE SAME

(75) Inventors: Tetsuji Imamura, Toyama (JP); Daisuke Kuwahara, Toyama (JP)

(73) Assignee: HOKURIKU ELECTRIC INDUSTRY CO., LTD., Toyama-Shi (JP)

( * ) Notice: Subject to any disclaimer, the term of this patent is extended or adjusted under 35 U.S.C. 154(b) by 278 days.

(21) Appl. No.: 13/500,236

(22) PCT Filed: Oct. 1, 2010

(86) PCT No.: PCT/JP2010/067232
§ 371 (c)(1),
(2), (4) Date: Apr. 4, 2012

(87) PCT Pub. No.: WO2011/043258
PCT Pub. Date: Apr. 14, 2011

(65) Prior Publication Data
US 2012/0193730 A1 Aug. 2, 2012

(30) Foreign Application Priority Data

Oct. 5, 2009 (JP) .................................. 2009-232006

(51) Int. Cl.
*H01L 29/66* (2006.01)
*H01L 21/02* (2006.01)
*H01L 29/78* (2006.01)
*G01N 27/12* (2006.01)

(52) U.S. Cl.
CPC ...................................... *G01N 27/12* (2013.01)

(58) Field of Classification Search
CPC .......... H01L 29/66; H01L 21/02; H01L 29/78
USPC .................... 257/414, 253; 438/49
See application file for complete search history.

(56) References Cited

U.S. PATENT DOCUMENTS

| 5,545,300 | A   | * | 8/1996  | Yun et al. ....................... 204/424 |
| 2006/0267202 | A1 | * | 11/2006 | Matsuzaki .................... 257/758 |
| 2009/0126460 | A1 | * | 5/2009  | Gardner et al. .............. 73/31.06 |

FOREIGN PATENT DOCUMENTS

| CN | 101021501 | 8/2007 |
| JP | 06-088802 | 3/1994 |

(Continued)

OTHER PUBLICATIONS

Chinese Office Action dated Jan. 16, 2013, 10 pages.

*Primary Examiner* — Evan Pert
*Assistant Examiner* — Damon Hillman
(74) *Attorney, Agent, or Firm* — Rankin, Hill & Clark LLP

(57) ABSTRACT

Provided herein are a gas sensor element in which deformation of a sensitive portion due to stress may be reduced and a method of manufacturing the gas sensor element. A base insulating layer 9 including a heater wiring pattern 19 is formed on a front surface 3A of a support 3. The base insulating layer 9 includes a fixed portion 15 fixed to the front surface 3A of the support 3, and a nonfixed portion 17 located over an opening portion 5. A cavity portion 7 having the opening portion 5 is formed in the support 3. An electrode wiring pattern 27 and a sensitive film 31 are formed over a central portion 21 of the nonfixed portion 17 of the base insulating layer 9. The nonfixed portion 17 includes the central portion 21 and a plurality of connecting portions 23 connecting the central portion 21 and the fixed portion 15. Four connecting portions 23 each include a base portion 33 and an extended portion 35. The base portion 33 of each connecting portion 23 is formed to extend along an edge portion 5A of the opening portion 5. Each extended portion 35 is formed to extend from the base portion 33 to the central portion 21 to be connected to the central portion 21. The connecting portions 23 are formed such that the maximum width W1 of each base portion 33 is larger than the maximum width W2 of each extended portions 35.

15 Claims, 19 Drawing Sheets

(56) References Cited

FOREIGN PATENT DOCUMENTS

| JP | 06-258268 | | 9/1994 |
| JP | 07-198646 | | 8/1995 |
| JP | 08-264844 | | 10/1996 |
| JP | 11-160267 | | 6/1999 |
| JP | 2000-258376 | | 9/2000 |
| JP | 2000258376 | * | 9/2000 |
| JP | 2007-132814 | | 5/2007 |
| JP | 2009-020053 | | 1/2009 |
| JP | 2009-058389 | | 3/2009 |

* cited by examiner

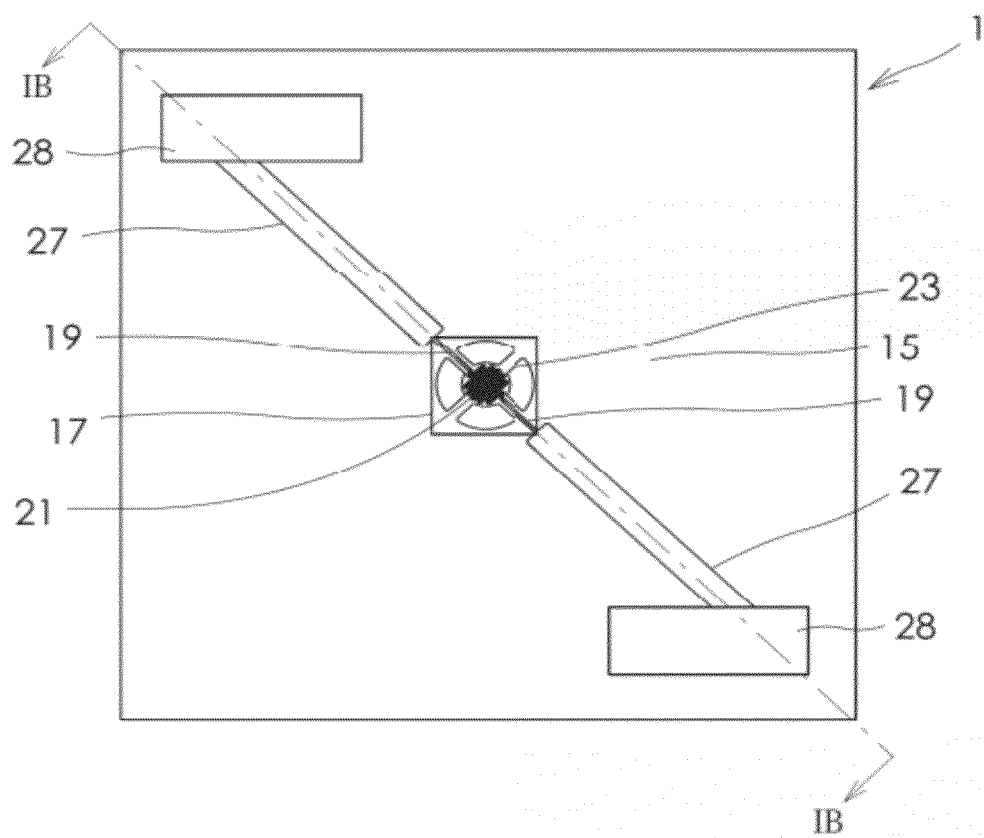

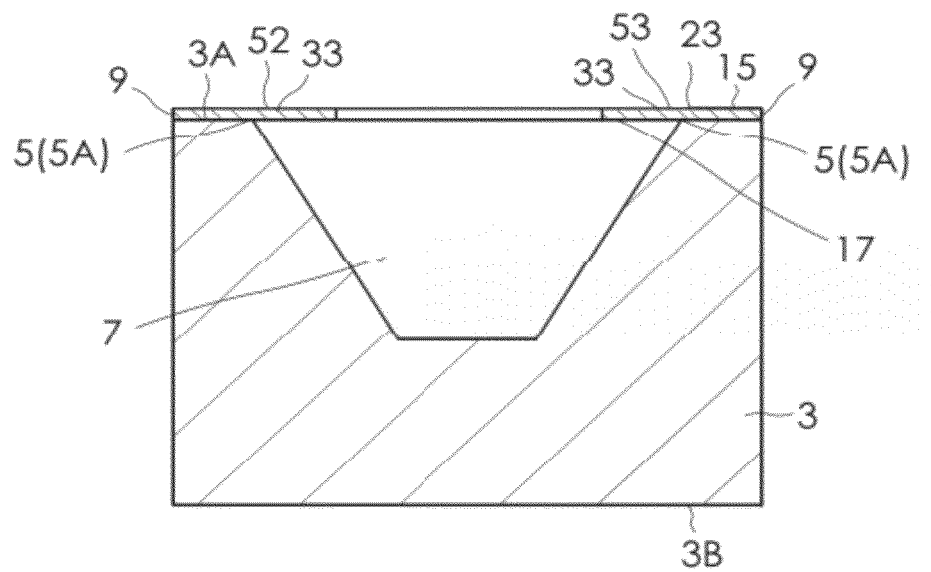

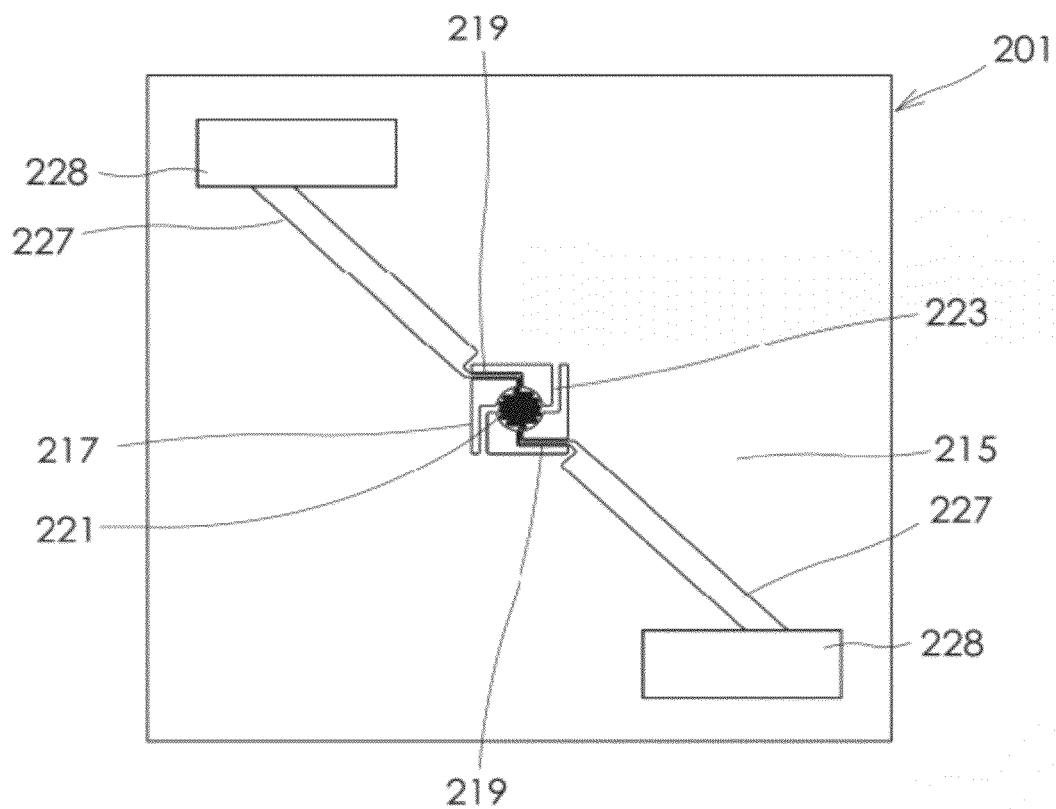

GAS SENSOR ELEMENT AND MANUFACTURING METHOD OF THE SAME

TECHNICAL FIELD

The present invention relates to a gas sensor element operable to detect gas, in which a sensitive portion including an electrode is formed on an insulator base including a heater therein.

BACKGROUND ART

Japanese Patent Application Publication No. 2007-132814 discloses a structure of a gas sensor element in which four bridges 3 disposed at equal intervals outside a stage 2 including a heater connect a silicon frame 1 and the stage 2. Japanese Patent Application Publication No. 2009-58389 discloses a structure of a gas sensor element in which a gas sensitive portion 11 including a detection electrode 12 is formed on an insulating layer 13 including heating means 14 (on a supported substrate portion 10), and a supporting substrate portion 30 mounted on a base member 31 and the supported substrate portion 10 with the gas sensitive portion 11 formed thereon are connected by bridge portions 20. The bridge portions 20 have an inverted swastika shape.

PRIOR ART DOCUMENTS

Patent Documents

Patent Document 1: Japanese Patent Application Publication No. 2007-132814
Patent Document 2: Japanese Patent Application Publication No. 2009-58389

OVERVIEW OF THE INVENTION

Technical Problem

In conventional gas sensor elements, the bridge portions (or bridges) are elaborately disposed as described above in order to absorb stress which may be generated at the sensitive portion. However, in the conventional gas sensor elements in which only the bridge portions (or bridges) are elaborately disposed, when a large stress is generated at the sensitive portion, the large stress cannot sufficiently be absorbed. Accordingly, deformation or breakage of the sensitive portion cannot be reduced.

An object of the present invention is to provide a gas sensor element in which deformation of a sensitive portion due to stress may be reduced, and a manufacturing method of the gas sensor element.

Another object of the present invention is to provide a gas sensor element which may readily be downsized and a manufacturing method of the gas sensor element.

Solution to Problem

A gas sensor element, the improvement of which is aimed at in the present invention, comprises: a support; a base insulating layer; a heater wiring pattern; an electrode wiring pattern; and a sensitive film. The support is formed of a silicon monocrystalline substrate, for example, and has a front surface and a back surface facing each other in a thickness direction of the support. A cavity portion is formed in the support, having an opening portion opened at least in the front surface. The base insulating layer is formed by laminating a plurality of insulating layers such as a lower insulating layer made of silicon nitride and silicon oxide and an upper insulating layer made of silicon nitride oxide. The base insulating layer includes: a fixed portion having a back surface fixed to the front surface of the support; and a nonfixed portion unitarily formed with the fixed portion and located over the opening portion of the support. The heater wiring pattern is formed inside the base insulating layer (between the lower insulating layer and the upper insulating layer) and includes an electric heater portion in a central portion of the nonfixed portion. The electrode wiring pattern is formed on a surface of the base insulating layer (specifically, the surface of the upper insulating layer) and includes a detecting electrode portion at the nonfixed portion. The sensitive film is formed by application over the detecting electrode portion at the central portion of the nonfixed portion. The nonfixed portion of the base insulating layer includes the central portion and four connecting portions connecting the central portion and the fixed portion.

In the present invention, the four connecting portions each include a base portion extending along an edge portion of the opening portion and an extended portion extending to be connected to the central portion. Preferably, the connecting portion is formed such that the maximum width of each base portion is larger than the maximum width each corresponding extended portion. Assume that the connecting portions of the nonfixed portion each include the base portion and the extended portion having such a dimensional relationship. If a large stress is generated due to heating at the nonfixed portion (central portion) of the base insulating layer including the heater therein and having the detecting electrode portion and the sensitive film formed on the surface thereof, the base portions of the connecting portions formed as described above absorb the stress generated at the central portion of the nonfixed portion, thereby positively reducing deformation and breakage of a sensitive portion including the detecting electrode portion and the sensitive film. Consequently, it is possible to obtain a gas sensor element whose sensor sensitivity cannot readily be lowered. The base portion having the maximum width larger than that of the extended portion may absorb stress generated at the central portion. Thus, the stress may be prevented from concentrating on the extended portion. Extended portions each connected to the central portion of the nonfixed portion are not directly connected to the fixed portion, but are connected to the fixed portion through the corresponding base portions for which the maximum width is larger than the maximum width for the extended portions. Thus the connecting portions may be strengthened or reinforced.

Preferably, the cavity portion of the support is formed such that the opening portion has a substantially square-shaped contour, and the base portions of the four connecting portions are located at four corners of the opening portion. If the cavity portion is formed as described above, the base portion of the connecting portion of the nonfixed portion may have the largest possible width.

Preferably, the base portions of the four connecting portions are each formed to extend across two sides out of four sides forming the edge portion of the opening portion, each two sides forming one of four corners of the opening portion. If the base portions of the four connecting portions are formed as described above, each base portion of the connecting portions may become larger in width away from the corresponding corner and have high mechanical strength since each base portion extends across two sides of the edge portion of the opening portion.

The nonfixed portion may have an arbitrary shape. For example, the central portion has a shape of a circular plate, and the extended portions of the four connecting portions extend along two virtual diagonal lines assumed for the four corners. The virtual diagonal lines herein mean two straight lines which are obtained by connecting the four corners of the substantially square-shaped opening portion in diagonal directions and which cross at the center of the opening portion. If the nonfixed portion is formed as described above, stress generated at the central portion of the nonfixed portion may be equally dispersed diagonally outwardly. (e.g., concentration of the stress at one of the extended portions may be prevented). The central portion may securely be connected to the fixed portion with a small number of the connecting portions, if the extended portions are formed as described above.

Alternatively, the nonfixed portion may have a central portion which has a shape of a circular plate, and that the extended portions of the connecting portions may each include a first extended portion and a second extended portion. The first extended section, in this case, is formed to extend along one of the sides of the edge portion of the substantially square-shaped opening portion, wherein one end of the first extended section is continuous with the base portion. The second extended section is formed to be continuous with the other end of the first extended portion, and extend to the central portion orthogonally to the first extended section. If the extended portions are formed to each include the first and second extended portions as described above, the extended portions each have a substantially swastika contour in the nonfixed portion. In other words, the extended portion of each connecting portion is bent at a right angle halfway between the central portion and the base portion of the nonfixed portion. Such arrangement may change the propagating direction of the stress generated at the central portion from a radial direction to a circumferential direction of the central portion, thereby enabling efficient absorption of the stress at both the extended portion and base portion.

Preferably, the nonfixed portion is formed such that edge portions of the base portions of the four connecting portions facing the central portion follow a virtual circle centering around the center of the central portion. Here, the virtual circle means a circle having an area larger than and similar in shape to a circle depicting the contour of the central portion of the circular plate shape centering around the center of the central portion. In this case, preferably, the central portion of the circular plate shape is formed to have a diameter of 0.1 to 0.7 times the diameter of the virtual circle. If the nonfixed portion is formed as described above, the stress generated at the central portion may equally be dispersed radially outwardly beyond the circumference of the central portion. Further, the size of each base portion (the area of the base portion as defined by the contour thereof) may be increased. In addition, the area of the central portion may be increased, thereby facilitating the formation of the sensitive film. Since the central portion has a circular surface, surface tension between the surface of the central portion and the applied sensitive film may likely be uniform. An amount of application of the sensitive film may be increased, and the thickness of the sensitive film to be formed over the surface of the central portion may be uniform. Assume that a ratio of the diameter of the central portion to the diameter of the virtual circle is smaller than 0.1 times. Then, the area of the central portion becomes relatively too small. Thus, it is impossible to secure an area for forming the detecting electrode and the sensitive film. Assume that the ratio of the diameter of the central portion to the diameter of the virtual circle is larger than 0.7 times. Then, the area of the base portions of the connecting portions becomes relatively too small. Thus, a large stress cannot be absorbed.

The cavity portion of the support may have an arbitrary shape. If the cavity portion of the support is formed to have a shape of a truncated square pyramid or a square pyramid whose cross-sectional area decreases from the opening portion toward the back surface of the support, the volume of the cavity portion may be reduced. The size of the gas sensor element may be reduced. Furthermore, the manufacturing cost of the gas sensor element may be reduced.

A manufacturing method of a gas sensor element of the present invention is described below. First, a silicon monocrystalline substrate having a front surface and a back surface facing each other in a thickness direction is prepared as a material of the support. The lower insulating layer is formed on the front surface of the silicon monocrystalline substrate. The heater wiring pattern is formed on a surface of the lower insulating layer such that the electric heater portion is formed on the surface of a portion of the lower insulating layer that forms the central portion of the nonfixed portion. The upper insulating layer is formed on the surface of the lower insulating layer to cover the heat wiring pattern. The base insulating layer is thus formed on the front surface of the silicon monocrystalline substrate. Then, the electrode wiring pattern is formed on the surface of the base insulating layer such that the detecting electrode portion is formed on the surface of a portion of the upper insulating layer of the base insulating layer that forms the nonfixed portion.

An etching resist film is then formed over the surface of the base insulating layer such that shapes of the fixed portion and the nonfixed portion remain in the surface of the base insulating layer. Then, the base insulating layer is etched by reactive ion etching until the front surface of the silicon monocrystalline substrate is exposed. Then, the connecting portions are formed such that the connecting portions each include a base portion extending along an edge portion of the opening portion and an extended portion extending from the base portion to the central portion to be connected to the central portion. Next, the cavity portion is formed by etching the exposed surface of the silicon monocrystalline substrate by anisotropic etching. The cavity portion is thus formed with the opening portion having a substantially square-shaped (roughly square) contour. The cavity portion having a shape of a truncated square pyramid or a square pyramid, whose cross-sectional area decreases from the opening portion toward the back surface of the support, is formed by this etching control. At least the etching resist film over the central portion is then removed to expose the detecting electrode portion, and the sensitive film is then formed over the detecting electrode portion on the surface of the central portion.

According to the manufacturing method of a gas sensor element as described above, it is possible to form the connecting portions including the base portions, which absorb stress generated at the central portion of the nonfixed portion, along the edge portion of the opening portion of the support merely by performing two-stage etching. That is, a gas sensor element, whose sensor sensitivity cannot readily be lowered, may be provided by the simple method. Particularly, the cavity portion is formed by performing the etching from the front surface of the support (the cavity portion is not formed by performing etching from the back surface of the support) in order to form a nonfixed portion of the base insulating layer. Thus, according to the manufacturing method of the present invention, a gas sensor element can be downsized.

BRIEF DESCRIPTION OF THE DRAWINGS

FIG. 1A is a diagram showing a first embodiment of a gas sensor element according to the present invention.

FIG. 3C is a sectional view taken along line IIIC-IIIC in FIG. 2A.

FIG. 8 is a diagram showing a third embodiment of a gas sensor element according to the present invention.

MODE FOR CARRYING OUT THE INVENTION

Figure 1B:
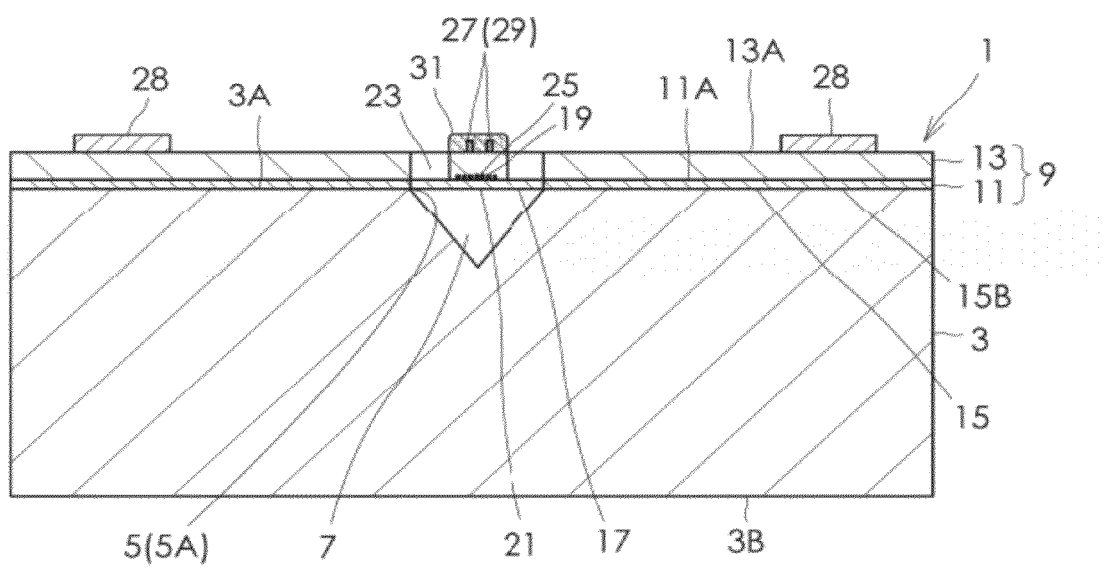
FIG. 1B is a sectional view taken along line IB-IB in FIG. 1A.
Figure 2A:
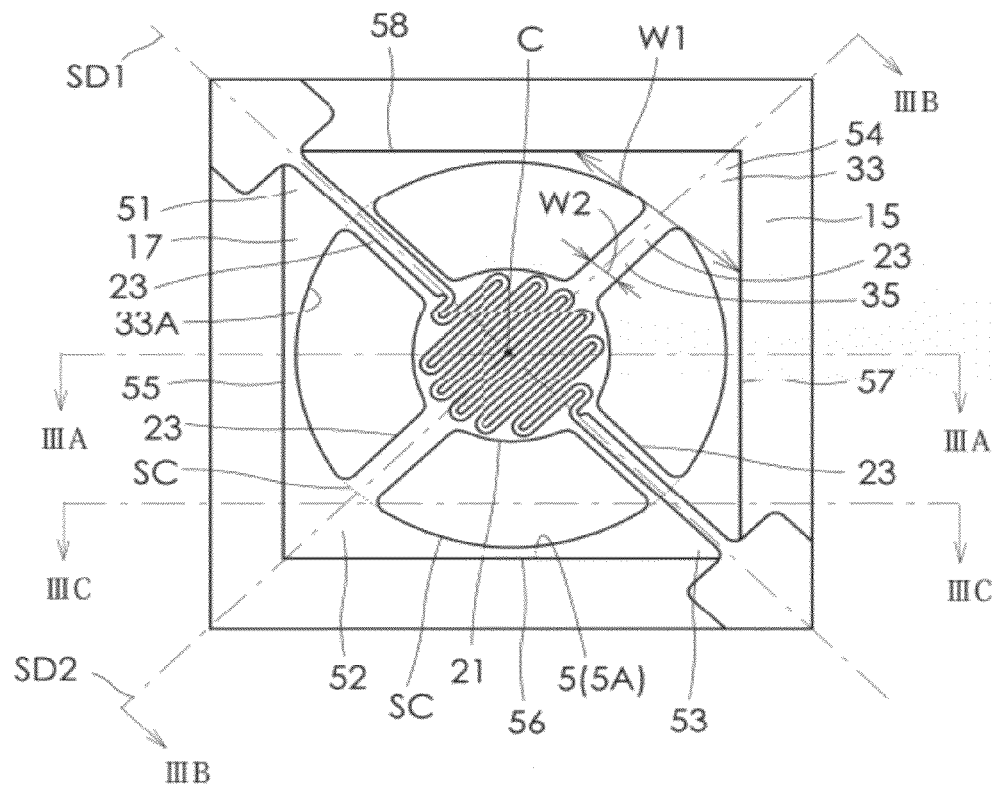
FIG. 2A is a diagram showing an enlarged view of a main portion of the gas sensor element shown in FIG. 1A.
Figure 2B:
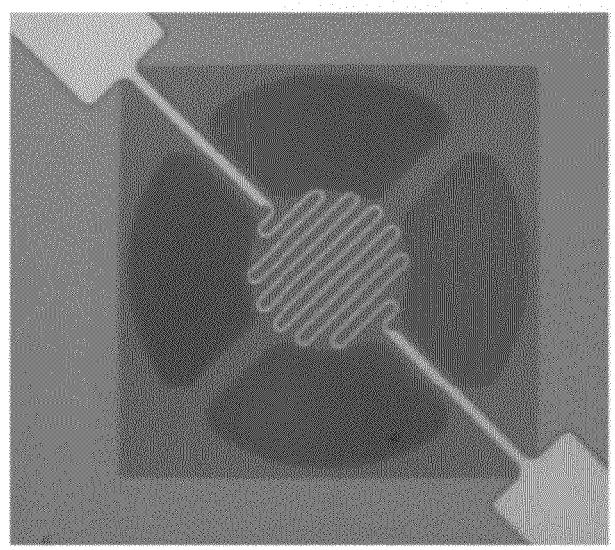
FIG. 2B is a scanning electron microscope (SEM) photograph corresponding to FIG. 2A showing an enlarged view of the main portion of the gas sensor element.
Figure 3A:
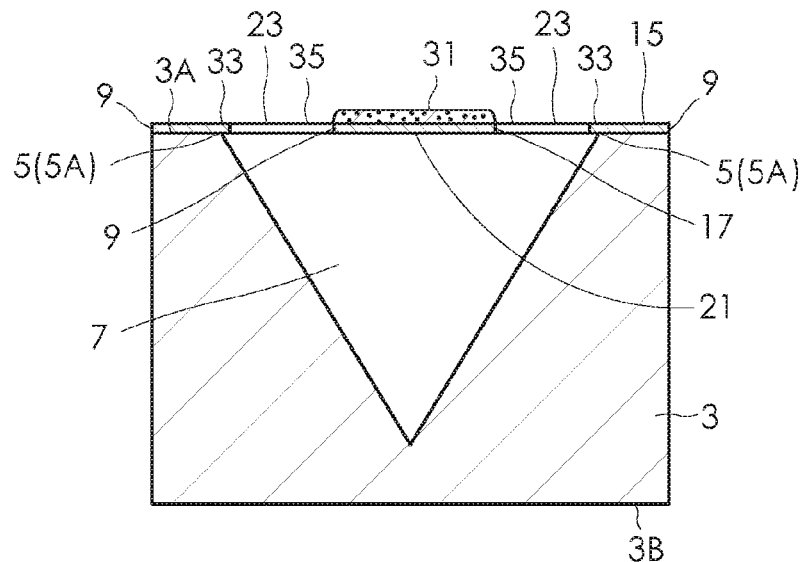
FIG. 3A is a sectional view taken along line IIIA-IIIA in FIG. 2A.
Figure 3B:
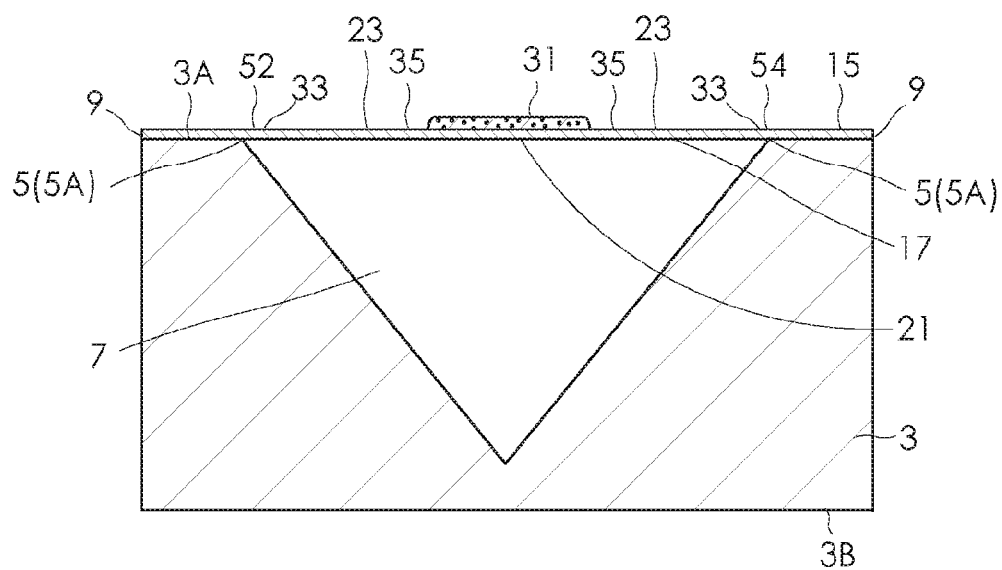
FIG. 3B is a sectional view taken along line IIIB-IIIB in FIG. 2A.

Embodiments of the present invention will be described below. FIG. 1A is a diagram showing a first exemplary embodiment of a gas sensor element according to the present invention, and FIG. 1B is a sectional view taken along line IB-IB in FIG. 1A. FIG. 2A is a diagram showing an enlarged view of a main portion of the gas sensor element in FIG. 1A, and FIG. 2B is a scanning electron microscope (SEM) photograph corresponding to FIG. 2A, taken at a magnification of 600×, showing an enlarged view of the main portion of the gas sensor element. FIG. 3A is a sectional view taken along line IIIA-IIIA in FIG. 2B. FIG. 3B is a sectional view taken along line IIIB-IIIB in FIG. 2B. FIG. 3C is a sectional view taken along line IIIC-IIIC in FIG. 2B. For facilitating understanding, a detecting electrode portion 29 and a sensitive film 31 which will be described later are omitted in FIGS. 2A and 3C. Further, referring to FIGS. 3A to 3C, a heater wiring pattern 19 and an electrode wiring pattern 27 (including the detecting electrode portion 29) are omitted. Referring to FIGS. 2A and 2B and FIGS. 3A to 3C, reference numeral 1 denotes the gas sensor element in the first embodiment. The gas sensor element 1 includes a support 3, a base insulating layer 9, the heater wiring pattern 19, the electrode wiring pattern 27, and a sensitive film 31.

The support 3 is formed of a silicon monocrystalline substrate which is 1.5 mm long, 1.5 mm wide, and 0.26 mm thick, and has a front surface 3A and a back surface 3B facing each other in a thickness direction of the support 3. A cavity portion 7 is formed in the support 3, having an opening portion 5 opened in the front surface 3A.

The base insulating layer 9 is formed by laminating a lower insulating layer 11 and an upper insulating layer 13 on the front surface 3A of the support 3 by plasma CVD. The lower insulating layer 11 is formed of a silicon oxide ($SiO_2$) layer which is 0.6 μm thick and a silicon nitride ($Si_3N_4$) layer which is 0.4 μm thick. The upper insulating layer 13 is made of silicon nitride oxide (SiON) and is 3 μm thick. The base insulating layer 9 includes a fixed portion 15 having a back surface 15B fixed to the front surface 3A of the support 3 and a nonfixed portion 17 unitarily formed with the fixed portion 15 and located over the opening portion 5 of the support 3. The nonfixed portion 17 includes a central portion 21 and four connecting portions 23 connecting the central portion 21 and the fixed portion 15.

The heater wiring pattern 19 is formed of a precious-metal thin-film layer which is 4000 Å thick, and is formed on a surface 11A of the lower insulating layer 11, being covered with the upper insulating layer 13. Then, the heater wiring pattern 19 includes an electric heater portion 25 in the central portion 21 of the nonfixed portion 17. The electric heater portion 25 has a function of heating the sensitive film 31 provided over the central portion 21, which will be described later, and volatizing a gas (impurity gas) not targeted for detection but attached to the sensitive film 31. A heating temperature of the electric heater portion 25 may be increased or decreased according to the type of the gas to be volatized.

The electrode wiring pattern 27 is made of Pt, includes the detecting electrode portion 29 at the nonfixed portion 17, and is formed on a surface 13A of the upper insulating layer 13 by sputtering. The electrode wiring pattern 27 is formed to be connected to an outside through a connecting electrode portion 28. The detecting electrode portion 29 has a function of detecting a change in resistance value of the gas sensor element 1 when a gas targeted for detection is attached to the sensitive film 31 which will be described later.

The sensitive film 31 is formed by applying a paste of a metal compound semiconductor mainly made of $In_2O_3$ over the detecting electrode portion 29 at the central portion 21 of the nonfixed portion 17, and then by firing at a temperature of 650° C. or higher. The sensitive film 31 absorbs the gas targeted for detection.

As shown in FIGS. 2A and 3A to 3C, the four connecting portions 23 each include a base portion 33 and an extended portion 35, in the first embodiment of the present invention. The base portion 33 of each connecting portion 23 is formed to extend along an edge portion 5A of the opening portion 5. Each extended portion 35 is formed to extend from the base portion 33 to the central portion 21 to be connected to the central portion 21. Then, the connecting portion is formed such that the maximum width W1 of each base portion 33 is larger than the maximum width W2 of the extended portion 35.

In other words, as shown in FIGS. 1B, 2A, and 3B, the opening portion 5 in the first embodiment of the present invention has a substantially square-shaped (roughly square)

contour, and the cavity portion 7 is formed in the support 3 such that the base portions 33 of the four connecting portions 23 are located at four corners 51, 52, 53, and 54 of the opening portion 5. If the cavity portion 7 of the support 3 is formed as described above, the base portions 33 may positively be formed at the nonfixed portion to absorb the stress which cannot fully be absorbed only by the extended portions 35. Further, the maximum width W1 of each base portion 33 of the nonfixed portion 17 may be increased as much as possible.

Further, the base portions 33 of the connecting portions 23 are formed at four corners 51 to 54 to respectively extend across two sides 55 and 58, 55 and 56, 56 and 57, and 57 and 58 out of the four sides 55, 56, 57, and 58 forming the edge portion 5A of the opening portion 5. If the base portions 33 are formed as described below, the base portions 33 may positively formed across over each two sides of the four sides of the edge portion 5. The base portions thus formed have a skirt-like shape having a wider hem and high mechanical strength.

In the first embodiment of the present invention, the central portion 21 of the nonfixed portion 17 has a shape of a circular plate, and the extended portions 35 of the four connecting portions 23 extend along two virtual diagonal lines SD1 and SD2 [two straight lines which are obtained by connecting the four corners 51 to 54 of the opening portion 5 in diagonal directions and which cross at the center (center C of the central portion 21) of the opening portion 5] assumed for the four corners 51 to 54. That is, the extended portions 35 of the four connecting portions 23 are formed to extend radially at substantially equal intervals (angle intervals of approximately 90°) from the central portion 21 to the base portions 33. Since the nonfixed portion 17 has such a shape, stress generated at the central portion 21 of the nonfixed portion 17 may be equally dispersed radially outwardly beyond the circumference of the central portion 21 (e.g., concentration of the stress at one of the extended portions may be prevented). Further, the central portion 23 may securely be connected to the fixed portion 15 with a small number of the connecting portions 23 (four connecting portions 23) if the extended portions 35 are formed as described above.

In the first embodiment of the present invention, the nonfixed portion 17 is formed such that edge portions 33A of the base portions 33 of the four connecting portions 23 facing the central portion 21 follow a virtual circle SC centering around the center C of the central portion (having an area larger than and substantially similar in shape to a circle depicting the contour of the central portion 21 of the circular plate shape centering around the center C of the central portion 21). The central portion 21 of the circular plate shape has a diameter of approximately 0.45 times (0.1 to 0.7 times) the diameter of the virtual circle, in this case. Since the edge portions 33A of the base portions 33 facing the central portion 21 of the circular plate shape form the shape of a circular plate centering around the same center C similar to the circular plate shape of the central portion 21, stress generated at the central portion 21 may be equally dispersed radially outwardly beyond the circumference of the central portion 21. Further, the size of each base portion 33 (the area of the base portion 33 as defined by the contour thereof) may be increased. In addition, the area of the central portion 21 may be increased. The sensitive film 31 is thereby readily formed. Surface tension between the surface of the central portion 21 of the circular plate shape and the applied sensitive film 21 are likely to be uniform. An amount of application of the sensitive film 31 may be therefore increased, and the film thickness of the sensitive film 31 to be formed over the surface of the central portion 21 may be uniform.

In the first embodiment of the present invention, the cavity portion 7 of the support 3 is formed such that the cavity portion 7 has a shape of a square pyramid whose cross-sectional area decreases more from the opening portion 5 toward the back surface 3B of the support 3, as shown in FIGS. 2A and 2B and FIGS. 3A to 3C. When the cavity of the gas sensor element is formed to have the shape of the square pyramid like the cavity portion 7, the volume of the cavity may be reduced. The size of the gas sensor element may be therefore reduced. Furthermore, the manufacturing cost of the gas sensor element may be reduced.

Figure 4:
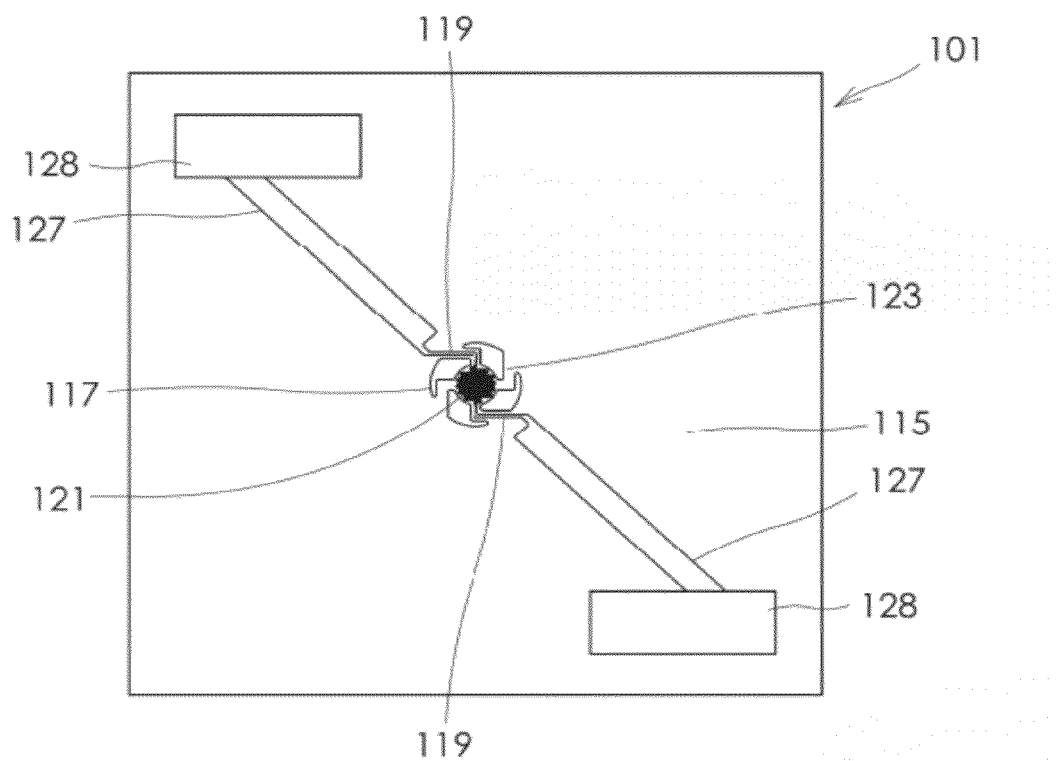
FIG. 4 is a diagram showing a second embodiment of a gas sensor element according to the present invention.
Figure 5A:
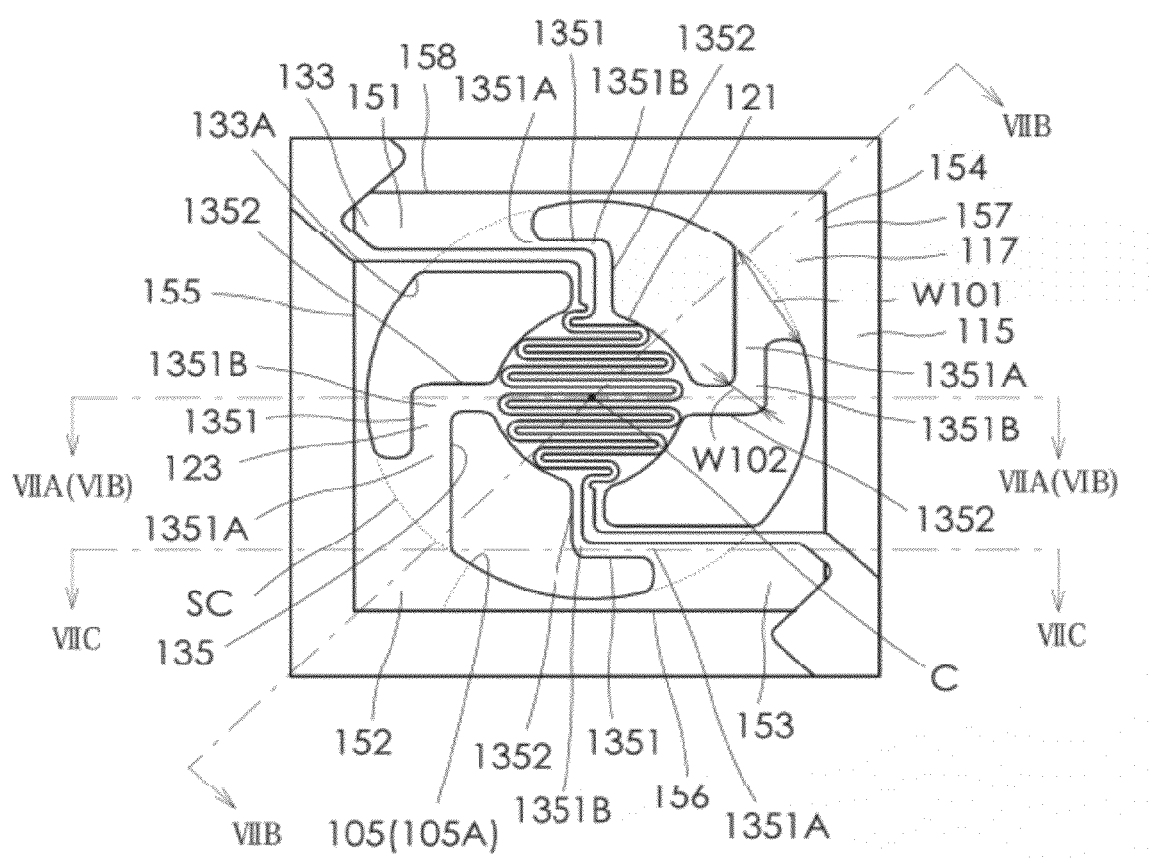
FIG. 5A is a diagram showing an enlarged view of a main portion of the gas sensor element in the second embodiment shown in FIG. 4.
Figure 5B:
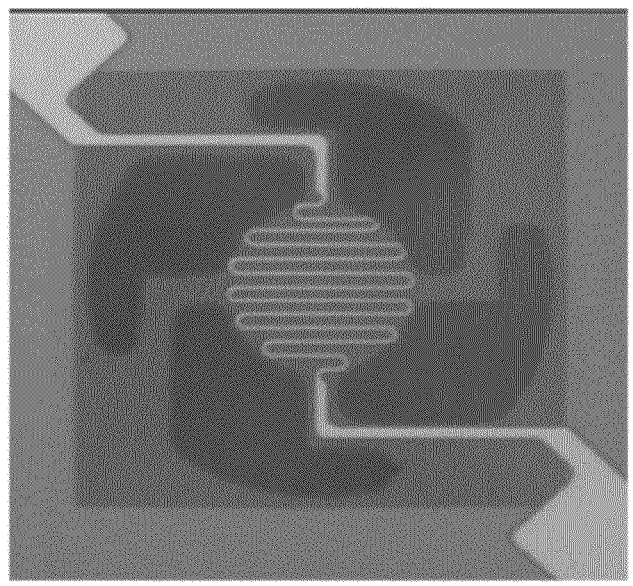
FIG. 5B is a SEM photograph corresponding to FIG. 5A showing an enlarged view of the main portion of the gas sensor element.
Figure 6:
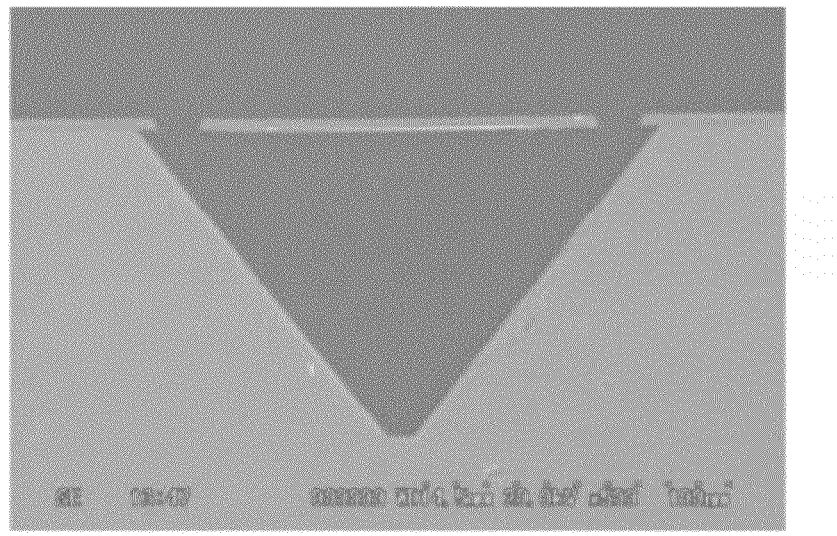
FIG. 6 is a SEM photograph showing an enlarged view of a main portion of the gas sensor element corresponding to a section taken along line VIB-VIB in FIG. 5A.
Figure 7A:
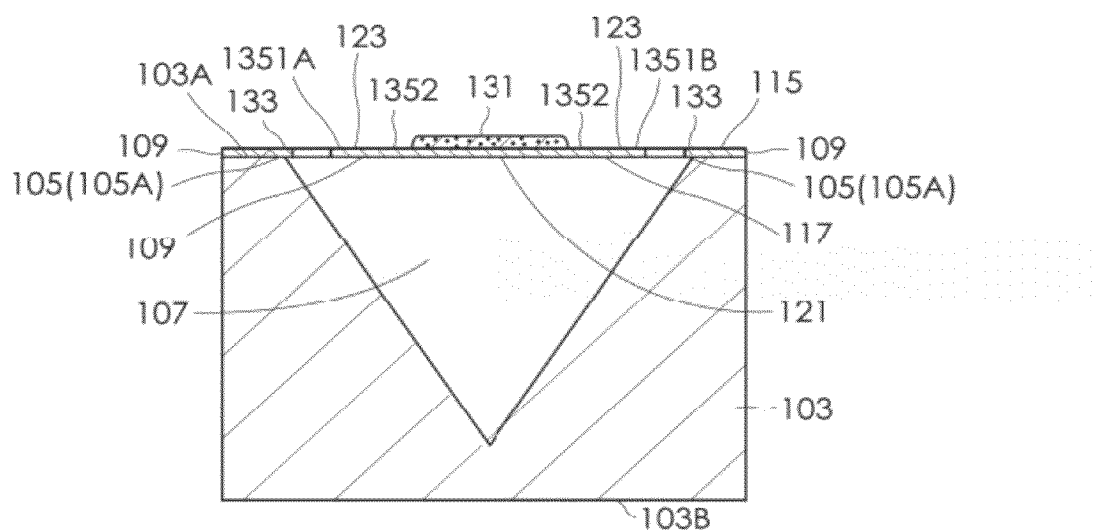
FIG. 7A is a sectional view taken along line VIIA-VIIA in FIG. 5A.
Figure 7B:
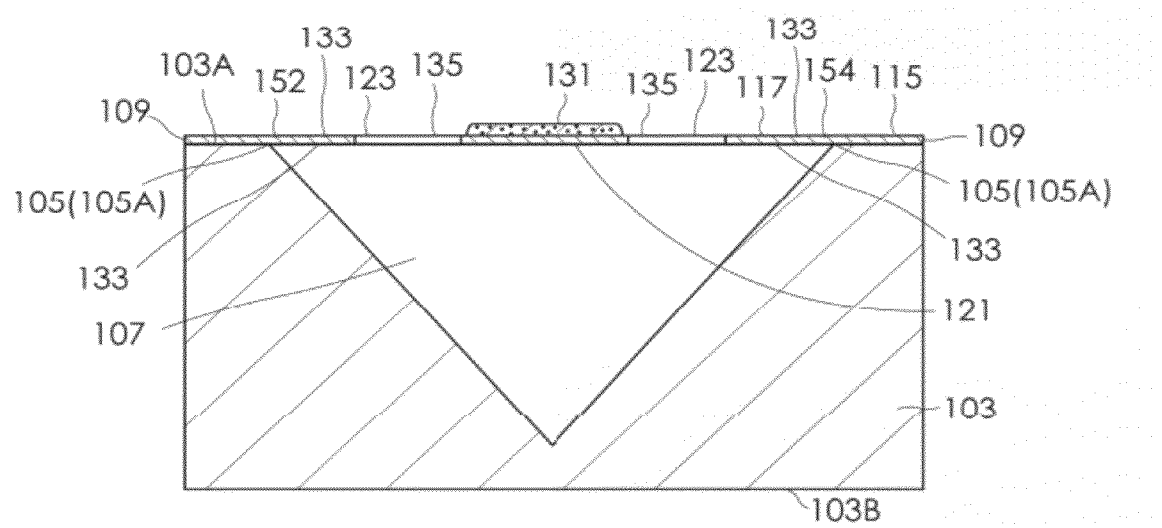
FIG. 7B is a sectional view taken along line VIIB-VIIB in FIG. 5A.
Figure 7C:
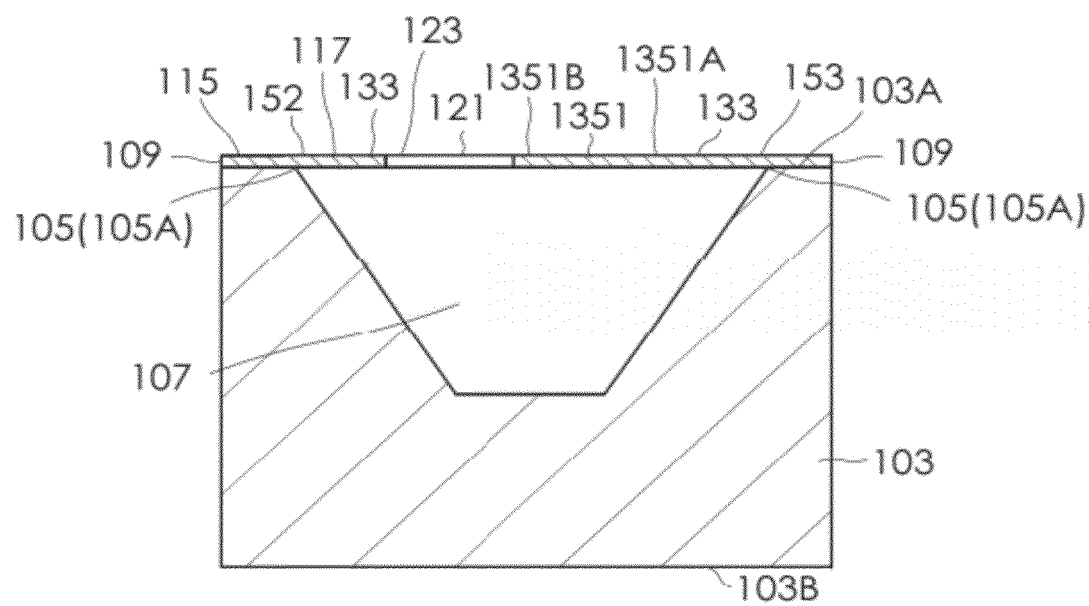
FIG. 7C is a sectional view taken along line VIIC-VIIC in FIG. 5A.

Next, a second embodiment of the present invention will be described. FIG. 4 is a diagram showing the second embodiment of a gas sensor element according to the present invention. FIG. 5A is a diagram showing an enlarged view of a main portion of the gas sensor element shown in FIG. 4. FIG. 5B is a SEM photograph corresponding to FIG. 5A, taken at a magnification of 400×, showing an enlarged view of the main portion of the gas sensor element. FIG. 6 is a SEM photograph, taken at a magnification of 500×, showing an enlarged view of a main portion of the gas sensor element corresponding to a section taken along line VIB-VIB in FIG. 5A. FIG. 7A is a sectional view taken along line VIIA-VIIA in FIG. 5A. FIG. 7B is a sectional view taken along line VIIB-VIIB in FIG. 5A. FIG. 7C is a sectional view taken along line VIIC-VIIC in FIG. 5A. Components in the second embodiment common to those in the first embodiment are given reference numerals obtained by adding 100 to the reference numerals allocated to the counterparts in the first embodiment, and description of the components in the second embodiment which are common to those in the first embodiment will be omitted. For facilitating understanding, a detecting electrode portion and a sensitive film 131 are omitted in FIGS. 4, 5A, and 7C. Further, a heater wiring pattern 119 and an electrode wiring pattern 127 (including the detecting electrode portion) are omitted in FIGS. 7A to 7C as well.

In the second embodiment of the present invention, a nonfixed portion 117 is shaped such that a central portion 121 has a shape of a circular plate and extended portions 135 of connecting portions 123 each include a first extended portion 1351 and a second extended portion 1352. The first extended portion 1351 is formed to extend along one of sides of an edge portion 105A of an opening portion 105 of a substantially square-shaped (roughly square) shape, wherein one end 1351A of the first extended portion 1351 is continuous with a base portion 133. Then, the second extended portion 1352 is formed to be continuous with the first extended portion 1351 and the other end 1351B of the first extended portion 1351, and to extend to the central portion 121 orthogonally to the first extended portion 1351. If the extended portion 135 of each connection portion 123 is formed to include the first and second extended portions 1351 and 1352 as described above, the extended portions 135 each have a substantially swastika contour in the nonfixed portion 117. In other words, the extended portion 135 of each connecting portion 123 is bent at a right angle halfway between the central portion 121 and the base portion 133 of the nonfixed portion 117. Such arrangement may change the propagating direction of the stress generated at the central portion 121 from a radial direction to a circumferential direction of the central portion 121, thereby enabling efficient absorption of the stress at both the extended portion 135 and the base portion 133 (refer to FIGS. 5A and 5B, FIG. 6, and FIGS. 7A to 7C).

Figure 9A:
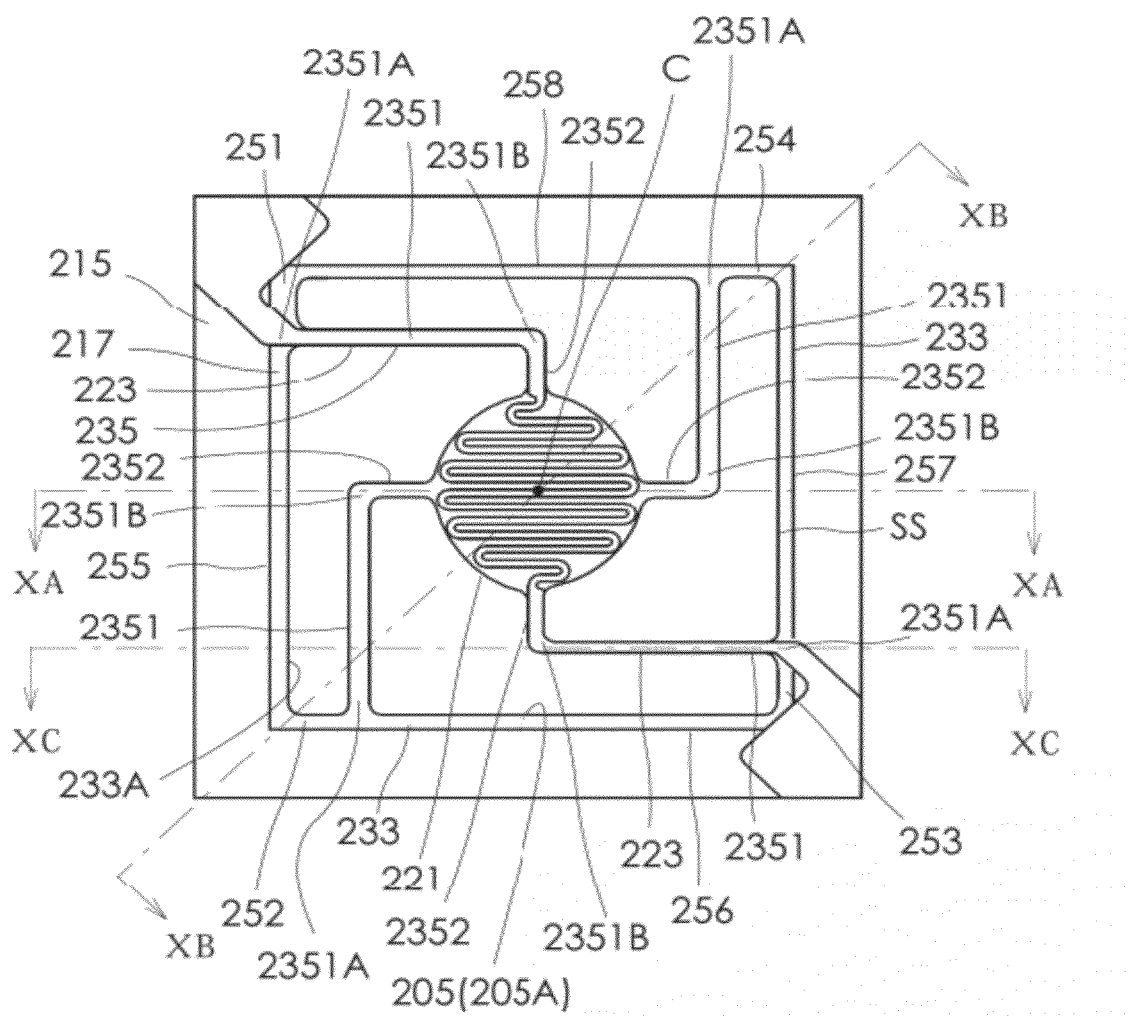
FIG. 9A is a diagram showing an enlarged view of a main portion of the gas sensor element in the third embodiment shown FIG. 8.
Figure 9B:
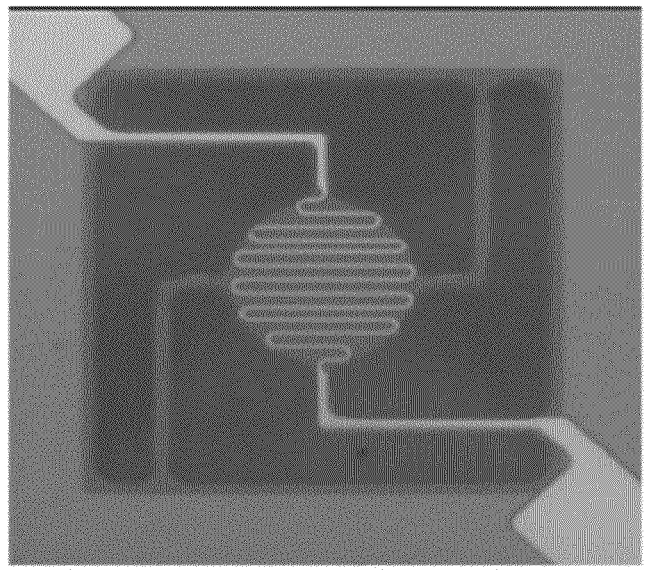
FIG. 9B is a SEM photograph corresponding to FIG. 9A showing an enlarged view of the main portion of the gas sensor element.
Figure 10A:
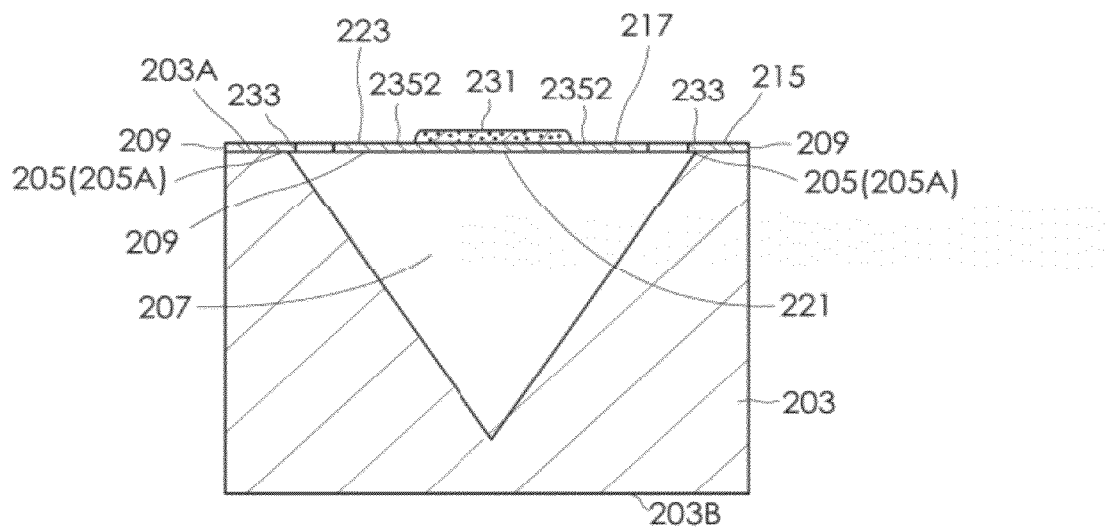
FIG. 10A is a sectional view taken along line XA-XA in FIG. 9A.
Figure 10B:
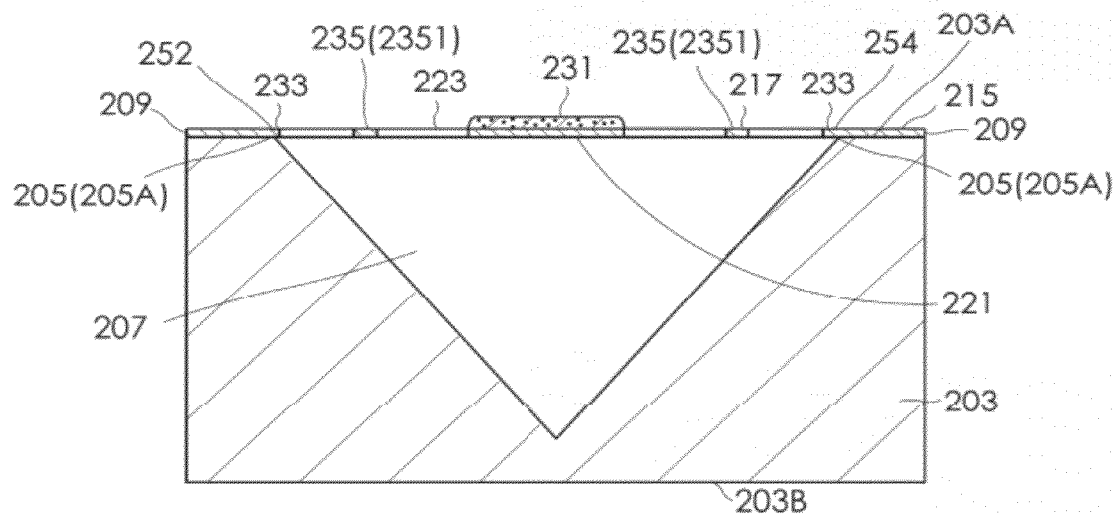
FIG. 10B is a sectional view taken along line XB-XB in FIG. 9A.
Figure 10C:
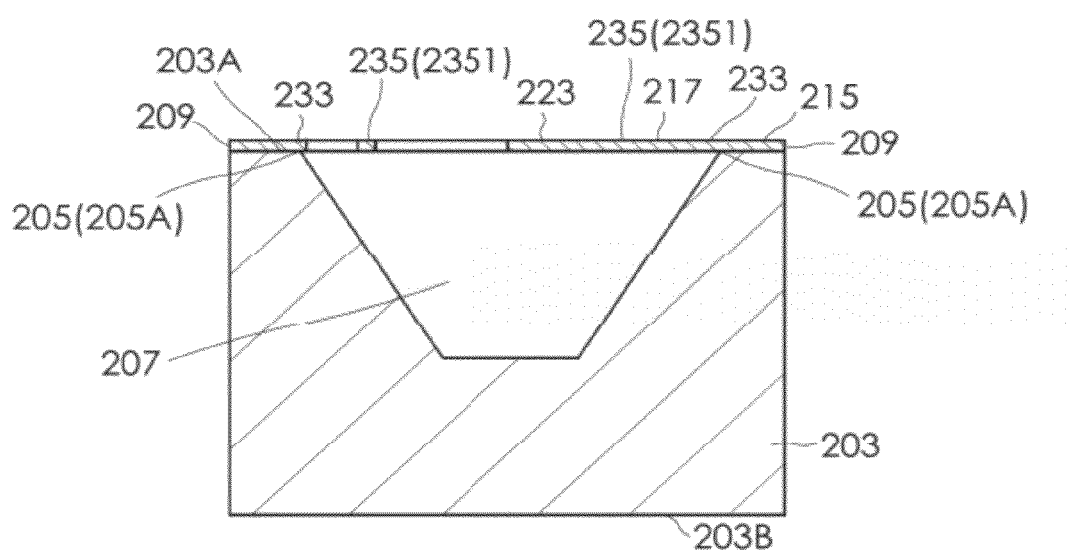
FIG. 10C is a sectional view taken along line XC-XC in FIG. 9A.

Next, a third embodiment will be described. FIG. 8 is a diagram showing the third embodiment of a gas sensor element according to the present invention. FIG. 9A is a diagram showing an enlarged view of a main portion of the gas sensor element shown FIG. 8, and FIG. 9B is a SEM photograph corresponding to FIG. 9A, taken at a magnification of 400×, showing an enlarged view of the main portion of the gas sensor element. FIG. 10A is a sectional view taken along line XA-XA in FIG. 9A. FIG. 10B is a sectional view taken along line XB-XB in FIG. 9A. FIG. 10C is a sectional view taken along line XC-XC in FIG. 9A. Components in the third embodiment common to those in the second embodiment are given reference numerals obtained by adding 100 to the reference numerals allocated to the counterparts in the second embodiment, and description of the components in the third embodiment which are common to those in the second embodiment will be omitted. For facilitating understanding, a detecting electrode portion and a sensitive film 231 are omitted in FIGS. 8, 9A, and 10C as well. Further, a heater wiring pattern 219 and an electrode wiring pattern 227 (including the detecting electrode portion) are omitted in FIGS. 10A to 10C as well.

In the third embodiment of the present invention as well, a nonfixed portion 217 is shaped such that a central portion 221 has a shape of a circular plate and extended portions 235 of connecting portions 223 each include a first extended portion 2351 and a second extended portion 2352. The third embodiment has a configuration common to that of the second embodiment in this respect. In the third embodiment, however, the nonfixed portion 217 is formed such that edge portions 233A of base portions 233 of four connecting portions 223 facing the central portion 221 extend along a virtual square SS centering around the center (center C of the central portion 221) of an edge portion 205A of an opening portion 205 of a support 203 (having an area smaller than and substantially similar in shape to a square depicting the contour of the edge portion 205A of the opening portion 205 of a square shape centering around the center C of the central portion 221). The third embodiment has a different configuration from that of the second embodiment in this respect. That is, the volume of each base portion 233 (the volume of the base portion 233 as defined by the contour) is thereby reduced. As shown in FIGS. 9A and 9B and FIGS. 10A to 10C, however, the third embodiment includes the base portions 233. Accordingly, as compared with a configuration where no base portions 233 are formed at the nonfixed portion 217 in FIG. 9A, stress, which cannot sufficiently be absorbed at the extended portions 235 (each including the first extended portion 2351 and the second extended portion 2352), may be absorbed at the base portions 233.

A method of manufacturing the gas sensor element in the first embodiment of the present invention as shown in FIG. 11 will be described, as an example of manufacturing method of a gas sensor element of the present invention. First, the silicon monocrystalline substrate 2 including a front surface 2A and a back surface 2B facing each other in the thickness direction is provided as a material of the support 3 (as shown in FIG. 11A). The lower insulating layer 11 formed of the silicon oxide ($SiO_2$) layer which is 6000 Å thick and the silicon nitride ($Si_3N_4$) layer which is 400 Å thick are formed on the front surface 2A of this silicon monocrystalline substrate 2 by Wet oxidation and LP-CVD (as shown in FIG. 11B). The heater wiring pattern 19 formed of the precious-metal thin-film layer, which is 4000 Å thick, is formed on the surface 11A of the lower insulating layer 11 such that the electric heater portion 25 is formed on the surface of a portion of the lower insulating layer 11 that forms the central portion 21 of the nonfixed portion 17 (as shown in FIG. 11C). The upper insulating layer 13 made of silicon nitride (SiON), which is 3 µm thick, is formed on the surface 11A of the lower insulating layer 11 by plasma CVD to cover the heat wiring pattern 19.

Figure 11A:
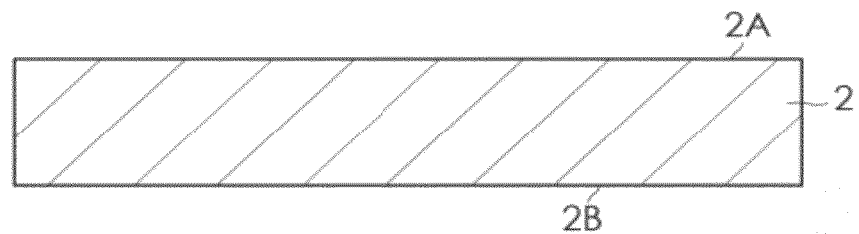
FIGS. 11A to 11H are process diagrams explaining an example of a manufacturing method of a gas sensor element of the present invention.
Figure 11B:
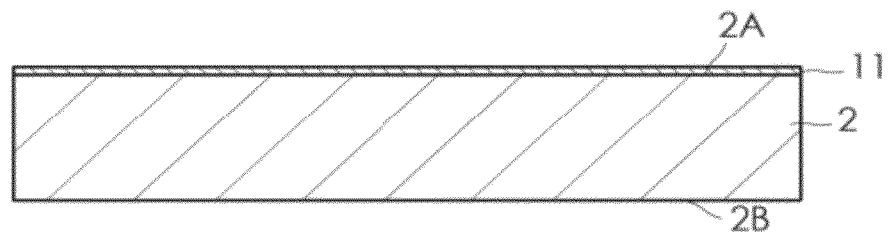
Figure 11C:
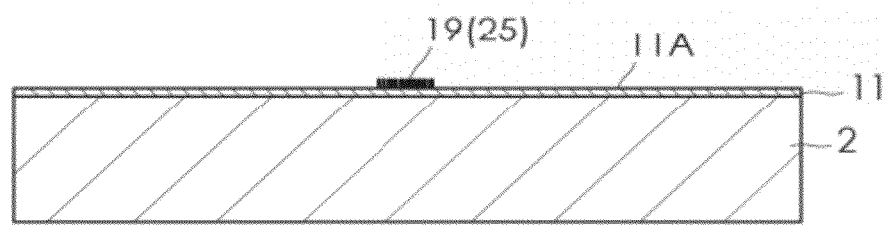
Figure 11D:
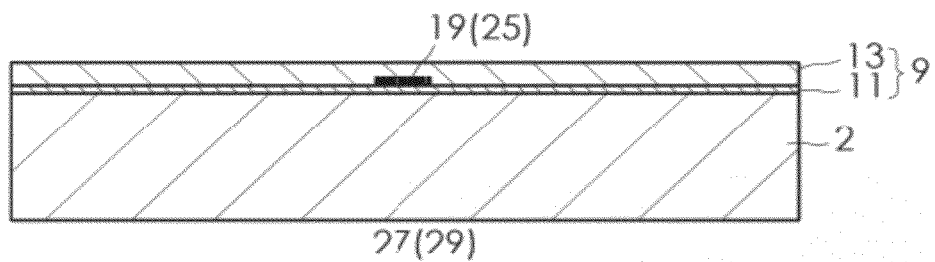
Figure 11E:
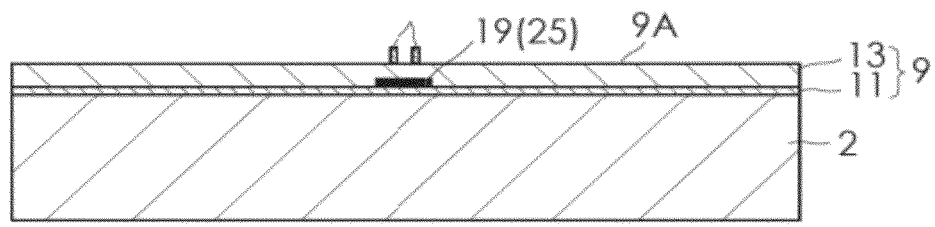

The base insulating layer 9 is thereby formed on the front surface 2A of the silicon monocrystalline substrate 2 (as shown in FIG. 11D). Then, the electrode wiring pattern 27 made of Pt is formed on the surface 9A of the base insulating layer 9 by sputtering such that the detecting electrode portion 29 is formed on the surface of a portion of the upper insulating layer 13 of the base insulating layer 9 that forms the nonfixed portion 17 (where the electric heater portion 25 has been formed), which will be described later (as shown in FIG. 11E).

Figure 11F:
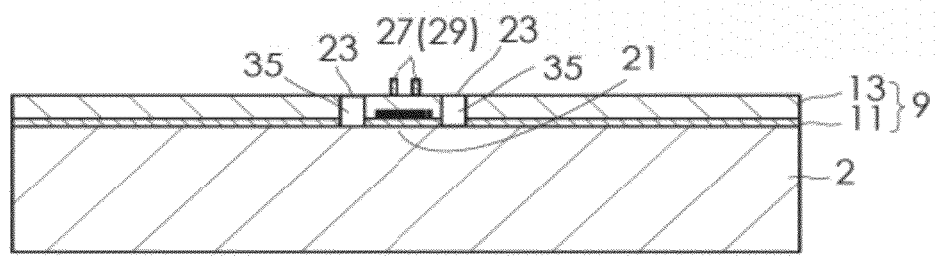

An etching resist film is then formed over the surface of the base insulating layer 9 such that shapes of the fixed portion and the nonfixed portion remain in the surface of the base insulating layer 9. Then, the base insulating layer 9 is etched by reactive ion etching until the front surface 2A of the silicon monocrystalline substrate 2 is exposed. Then, the connecting portions 23 are formed such that the connecting portions 23 each include the base portion 33, which will be described later, extending along the edge portion 5A of the opening portion 5, which will be described later, and the extended portion 35 extending from the base portion 33 to the central portion 21 to be connected to the central portion 21 (as shown in FIG. 11F).

Figure 11G:
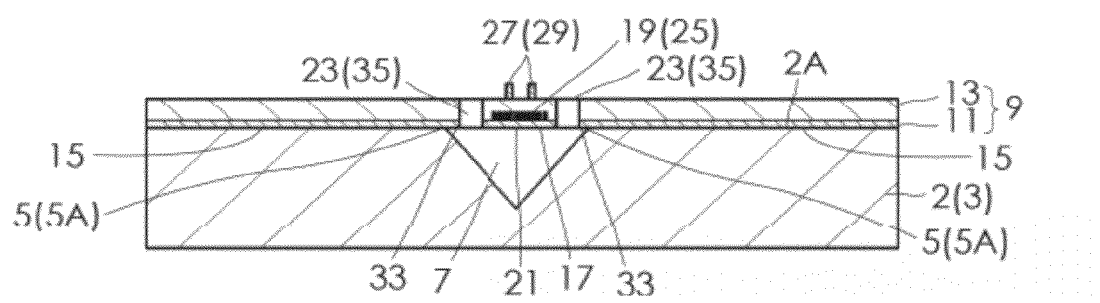
Figure 11H:
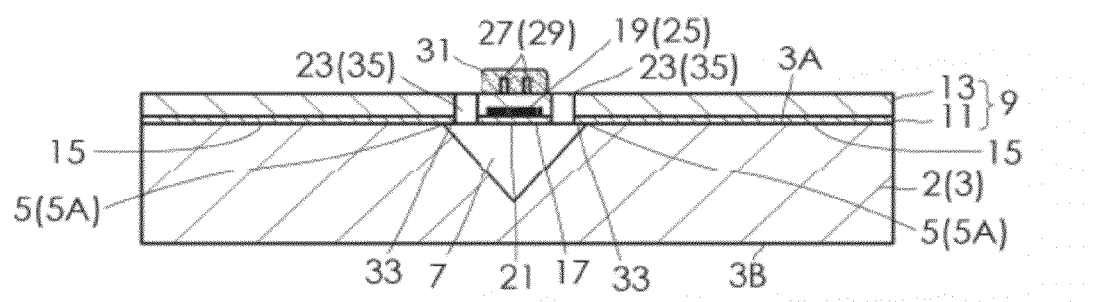

Next, the cavity portion 7 is formed by etching the exposed surface 2A of the silicon mono crystalline substrate 2 by anisotropic etching. The cavity portion is thereby formed with the opening portion 5 having the substantially square-shaped (roughly square) contour. The cavity portion 7 having the shape of the square pyramid, whose cross-sectional area decreases from the opening portion 5 toward the back surface 3B of the support 3, is formed by this etching control to form the support 3 (as shown in FIG. 11G). Specifically, the cavity portion 7 having the shape of the square pyramid is formed in the surface 2A of the silicon monocrystalline substrate 2 such that the base portions 33 of the four connecting portions 23 are located at the four corners 51 to 54 of the opening portion 5, and the base portions 33 are formed to extend across the two sides 55 and 58, 55 and 56, 56 and 57, 57 and 58 out of the four sides 55 to 58 forming the edge portion 5A of the opening portion 5. The support 3 is thereby formed. Then, the etching resist film over the central portion 21 is removed to expose the detecting electrode portion 29. The sensitive film 31 is then formed over the detecting electrode portion 29 on the surface of the central portion 21. The sensitive film 31 is formed by applying the paste of the metal compound semiconductor mainly made of $In_2O_3$ over the surface of the central portion 21, and then by firing at the temperature of 650° C. or higher (as shown in FIG. 11H).

According to the manufacturing method of a gas sensor element as described above, it is possible to form the connecting portions 23 including the base portions 33, which absorb stress generated at the central portion 21 of the nonfixed portion 17, along the edge portion 5A of the opening portion 5 of the support 3 merely by performing two-stage etching. That is, a gas sensor element, whose sensor sensitivity cannot readily be lowered, may be provided by the simple method. Particularly, the cavity portion is formed by performing the etching from the front surface of the support (the cavity portion is not formed by performing etching from the back surface of the support) in order to form a nonfixed portion of the base insulating layer. Thus, according to the manufacturing method of the present invention, a gas sensor element can be downsized.

The present invention is not limited to these embodiments, and modifications are of course possible within the scope of the technical concept of the present invention.

INDUSTRIAL APPLICABILITY

According to the present invention, the connecting portions of the nonfixed portion each include the base portion and the extended portion. Accordingly, even if a large stress has been generated due to heating at the nonfixed portion (central portion) of the base insulating layer including the heater and having the detecting electrode portion and the sensitive film formed on the surface thereof, the base portions of the connecting portions formed along the edge portion of the opening portion of the support absorb the stress generated at the central portion of the nonfixed portion. Deformation and breakage of a sensitive portion including the detecting electrode portion and the sensitive film may positively be reduced. Accordingly, a gas sensor element, whose sensor sensitivity cannot readily be lowered, may be provided.

The base portion having the maximum width larger than that of the extended portion may absorb stress generated at the central portion, thereby preventing the stress from concentrating on the extended portion. Each extended portion connected to the central portion of the nonfixed portion is not directly connected to the fixed portion, but is connected to the fixed portion through the base portion whose maximum width is larger than that of the extended portion. Thus, strength of the connecting portion may be increased.

Further, the cavity portion (opening portion) is formed in the front surface of the support (and is not formed in the back surface of the support) in order to form the nonfixed portion of the base insulting layer. Accordingly, the gas sensor element may be downsized and gas sensor element may readily be formed.

EXPLANATION OF SYMBOLS 1, 101, 201 gas sensor element
2 silicon monocrystalline substrate
3, 103, 203 support
3A front surface
3B, 103B, 203B back surface
5, 105, 205 opening portion
5A, 105A, 205A edge portion
7, 107, 207 cavity portion
9 base insulating layer
11 lower insulating layer
11A surface
13 upper insulating layer
13A surface
15 fixed portion
17, 117, 217 nonfixed portion
19, 119 heater wiring pattern
21, 121, 221 central portion
C center
23, 123, 223 connecting portion
25 electric heater portion
27, 127 electrode wiring pattern
29, 129 detecting electrode portion
31, 131 sensitive film
33, 133, 233 base portion
33A, 133A, 233A edge portion
SC virtual circle
35, 135, 235 extended portion
1351, 2351 first extended portion
1351A, 2351A one end
1351B, 2351B the other end
1352, 2352 second extended portion
51, 52, 53, 54 four corners
55, 56, 57, 58 four sides
SD1, SD2 virtual diagonal lines

The invention claimed is:

1. A gas sensor element comprising:
a support formed of a silicon monocrystalline substrate and having a front surface and a back surface facing each other in a thickness direction of the support, wherein a cavity portion is formed in the support, having an opening portion opened at least in the front surface;
a base insulating layer formed by laminating a lower insulating layer made of silicon nitride and silicon oxide and an upper insulating layer made of silicon nitride oxide, the base insulating layer including:
a fixed portion having a back surface fixed to the front surface of the support; and
a nonfixed portion unitarily formed with the fixed portion and located over the opening portion of the support;
a heater wiring pattern formed between the lower insulating layer and the upper insulating layer and including an electric heater portion formed on and in contact with a central portion of the nonfixed portion, the central portion having a shape as a circular plate;
an electrode wiring pattern formed on a surface of the upper insulating layer and including a detecting electrode portion at the nonfixed portion; and
a sensitive film formed by application over the detecting electrode portion at the central portion of the nonfixed portion; and,
the nonfixed portion of the base insulating layer including the central portion and four connecting portions connecting the central portion and the fixed portion;
the connecting portions each including a base portion extending along an edge portion of the opening portion and an extended portion extending to be connected to the central portion, wherein:
the base portions of the four connecting portions are located at four corners of the opening portion, and the base portions are each formed to extend across two sides out of four sides forming the edge portion of the opening portion, each two sides forming one corner of the opening portion corresponding to one base portion; and,
edge portions of the base portions of the four connecting portions facing the central portion follow a virtual circle centering around the center of the central portion.

2. The gas sensor element according to claim 1, wherein:
the extended portions of the four connecting portions extend along two virtual diagonal lines assumed for the four corners.

3. The gas sensor element according to claim 1, wherein:
the extended portions of the connecting portions each including:
a first extended section extending along one of the sides of the edge portion of the substantially squared-shaped opening portion, wherein one end of the first extended section is continuous with the base portion; and
a second extended section continuous with the other end of the first extended portion, and extending to the central portion orthogonally to the first extended section.

4. A gas sensor element comprising:
a support having a front surface and a back surface facing each other in a thickness direction of the support, wherein a cavity portion is formed in the support, having an opening portion opened at least in the front surface;
a base insulating layer formed by laminating a plurality of insulating layers, the base insulating layer including:
a fixed portion having a back surface fixed to the front surface of the support; and
a nonfixed portion unitarily formed with the fixed portion and located over the opening portion;

a heater wiring pattern formed inside the base insulating layer and including an electric heater portion formed on and in contact with a central portion of the nonfixed portion, the central portion having a shape of a circular plate;

an electrode wiring pattern formed on a surface of the base insulating layer and including a detecting electrode portion at the nonfixed portion; and a sensitive film formed over the detecting electrode portion at the central portion of the nonfixed portion;

the nonfixed portion of the base insulating layer including the central portion and a plurality of connecting portions connecting the central portion and the fixed portion;

the connecting portions each including a base portion extending along an edge portion of the opening portion and an extended portion extending to be connected to the central portion, wherein the maximum width of each base portion is larger than the maximum width of each corresponding extended portion; and, edge portions of the base portions of the four connecting portions facing the central portion following a virtual circle centering around the center of the central portion.

5. The gas sensor element according to claim 4, wherein:
the opening portion has a substantially square-shaped contour; and
the base portions of four connecting portions out of the connecting portions are located at four corners of the opening portion.

6. The gas sensor element according to claim 5, wherein the base portions are each formed to extend across two sides out of four sides forming the edge portion of the opening portion, each two sides forming one corner of the opening portion corresponding to one base portion.

7. The gas sensor element according to claim 5, wherein:
the extended portions of the four connecting portions extend along two virtual diagonal lines assumed for the four corners.

8. The gas sensor element according to claim 5, wherein:
the extended portions of the connecting portions each including:
a first extended section extending along one of the sides of the edge portion of the substantially square-shaped opening portion, wherein one end of the first extended section is continuous with the base portion; and
a second extended section continuous with the other end of the first extended portion, and extending to the central portion orthogonally to the first extended section.

9. The gas sensor element according to claim 4, wherein:
the central portion having the shape of a circular plate has a diameter of 0.1 to 0.7 times a diameter of the virtual circle.

10. The gas sensor element according to claim 4, wherein the cavity portion has a shape of a truncated square pyramid or a square pyramid whose cross-sectional area decreases from the opening portion toward the back surface of the support.

11. A manufacturing method of a gas sensor element that comprises:
a support formed of a silicon monocrystalline substrate and having a front surface and a back surface facing each other in a thickness direction of the support, wherein a cavity portion is formed in the support, having an opening portion opened at least in the front surface;
a base insulating layer formed by laminating a lower insulating layer made of silicon nitride and silicon oxide and an upper insulating layer made of silicon nitride oxide, the base insulating layer including:
a fixed portion having a back surface fixed to the front surface of the support; and
a nonfixed portion unitarily formed with the fixed portion and located over the opening portion, the nonfixed portion of the base insulating layer including a central portion and four connecting portions connecting the central portion and the fixed portion, the central portion having a shape of a circular plate;
a heater wiring pattern formed inside the base insulating layer and including an electric heater portion formed on and in contact with the central portion of the nonfixed portion;
an electrode wiring pattern formed on a surface of the upper insulating layer and including a detecting electrode portion at the nonfixed portion; and
a sensitive film formed by application over the detecting electrode portion at the central portion of the nonfixed portion, the method comprising:
providing a silicon monocrystalline substrate having a front surface and a back surface facing each other in a thickness direction, as a material of the support;
forming the base insulating layer on the front surface of the silicon monocrystalline substrate, by following the steps of:
forming the lower insulating layer on the front surface of the silicon monocrystalline substrate,
forming the heater wiring pattern on a surface of the lower insulating layer such that the electric heater portion is formed on the surface of a portion of the lower insulating layer that forms the central portion of the nonfixed portion, and
forming the upper insulating layer on the surface of the lower insulating layer to cover the heater wiring pattern;
forming the electrode wiring pattern on the surface of the base insulating layer such that the detecting electrode portion is formed on the surface of a portion of the upper insulating layer of the base insulating layer that forms the nonfixed portion;
forming the connecting portions such that the connecting portions each include a base portion extending along an edge portion of the opening portion and an extended portion extending to be connected to the central portion, by following the steps of:
forming an etching resist film over the surface of the base insulating layer such that shapes of the fixed portion and the nonfixed portion remain in the surface of the base insulating layer, and
etching the base insulating layer by reactive ion etching until the front surface of the silicon monocrystalline substrate is exposed;
forming the cavity portion and the nonfixed portion in the monocrystalline substrate by etching the exposed surface of the silicon monocrystalline substrate by anisotropic etching, the cavity portion formed with the opening portion having a substantially square-shaped contour, and having a shape of a truncated square pyramid or a square pyramid whose cross-sectional area decreases from the opening portion toward the back surface of the support, and the nonfixed portion formed with edge portions of the base portions of the four connecting portions facing the central portion following a virtual circle centering around the center of the central portion; and
forming the sensitive film over the detecting electrode portion on the surface of the central portion after removing the etching resist film formed at least over the central portion to expose the detecting electrode portion.

12. The gas sensor element according to claim 1, wherein:
the central portion has a diameter of 0.1 to 0.7 times a diameter of the virtual circle.

13. The gas sensor element according to claim 7, wherein:
the central portion has a diameter of 0.1 to 0.7 times a diameter of the virtual circle.

14. The gas sensor element according to claim 8, wherein:
the central portion has a diameter of 0.1 to 0.7 times a diameter of the virtual circle.

15. The gas sensor element according to claim 1, wherein the cavity portion has a shape of a truncated square pyramid or a square pyramid whose cross-sectional area decreases from the opening portion toward the back surface of the support.

* * * * *